US008728397B2

(12) United States Patent
Richardson

(10) Patent No.: US 8,728,397 B2
(45) Date of Patent: May 20, 2014

(54) SUBSTANCE DETECTION DEVICE UTILIZING A CYCLONE PARTICLE SEPARATOR

(75) Inventor: Stephen Richardson, London (GB)

(73) Assignee: Smith Detection-Watford Limited, Herts (GB)

( * ) Notice: Subject to any disclaimer, the term of this patent is extended or adjusted under 35 U.S.C. 154(b) by 352 days.

(21) Appl. No.: 12/747,318

(22) PCT Filed: Dec. 11, 2008

(86) PCT No.: PCT/IB2008/003789
§ 371 (c)(1), (2), (4) Date: Sep. 7, 2010

(87) PCT Pub. No.: WO2009/074877
PCT Pub. Date: Jun. 18, 2009

(65) Prior Publication Data
US 2011/0001045 A1 Jan. 6, 2011

(30) Foreign Application Priority Data
Dec. 11, 2007 (GB) .................. 0724127.6

(51) Int. Cl.
*G01N 33/00* (2006.01)
*G01N 1/22* (2006.01)
*B04C 5/00* (2006.01)
(52) U.S. Cl.
USPC ........... 422/68.1; 209/715; 209/717; 209/722
(58) Field of Classification Search
USPC ........... 422/613, 50, 68.1; 209/715, 716, 717, 209/720, 721, 722, 724, 725; 324/464
See application file for complete search history.

(56) References Cited

U.S. PATENT DOCUMENTS

| 3,070,990 A | 1/1963 | Stanley |
| 3,385,437 A | 5/1968 | Woodruff |

(Continued)

FOREIGN PATENT DOCUMENTS

| EP | 0 447 158 A1 | 9/1991 |
| GB | 2 254 024 A | 9/1922 |
| GB | 1 053 159 A | 12/1966 |
| WO | WO 2006/079773 A | 8/2006 |

OTHER PUBLICATIONS

Brouwer, E. R. et al. "Use of Membrane Extraction Disks for On-Line Trace Enrichment of Organic Compounds from Aqueous Samples." Chromatographia (1990) 29 415-418.*

(Continued)

*Primary Examiner* — Christopher A Hixson
(74) *Attorney, Agent, or Firm* — Foley & Lardner LLP

(57) ABSTRACT

A substance detection device, including a chemical substance analyzer, including an ion mobility spectrometer (IMS), a desorber, a conduit, and a membrane. The membrane extends across a cross-section of the conduit, and the membrane is positioned to have a desorber side in gas communication with the desorber and an analysis side opposite the desorber side. The substance detection device can be configured to direct a portion of a chemical substance to the desorber through the conduit so that at least a portion of the entrained chemical substance is transferred to the membrane by interacting with the desorber side of the membrane. The membrane is adapted to diffuse at least a portion of the chemical substance transferred to the membrane through the membrane to the analysis side. The device also includes a particle separator including a protuberance extending into a collection chamber of the particle separator.

20 Claims, 3 Drawing Sheets

(56) References Cited

U.S. PATENT DOCUMENTS

| | | |
|---|---|---|
| 2002/0078826 A1 | 6/2002 | Day et al. |
| 2002/0157993 A1 | 10/2002 | Call et al. |
| 2003/0033890 A1 | 2/2003 | Rodgers |

OTHER PUBLICATIONS

Baumbach, J. I. "Process analysis using ion mobility spectrometry." Anal. Bioanal. Chem. (2006) 384 1059-1070.*

Karlsson, Anders et al. "Single-Stage Flowing Liquid Film Impactor for Continuous On-Line Particle Analysis." J. Aerosol Sci. (1997) 28 1539-1551.*

Willeke, Klaus et al. "Improved Aerosol Collection by Combined Impaction and Centrifugal Motion." Aerosol Science and Technology (1998) 28 439-456.*

International Search Report for International Application No. PCT/IB2008/003789; mail date Jun. 16, 2009, 3 pages.

* cited by examiner

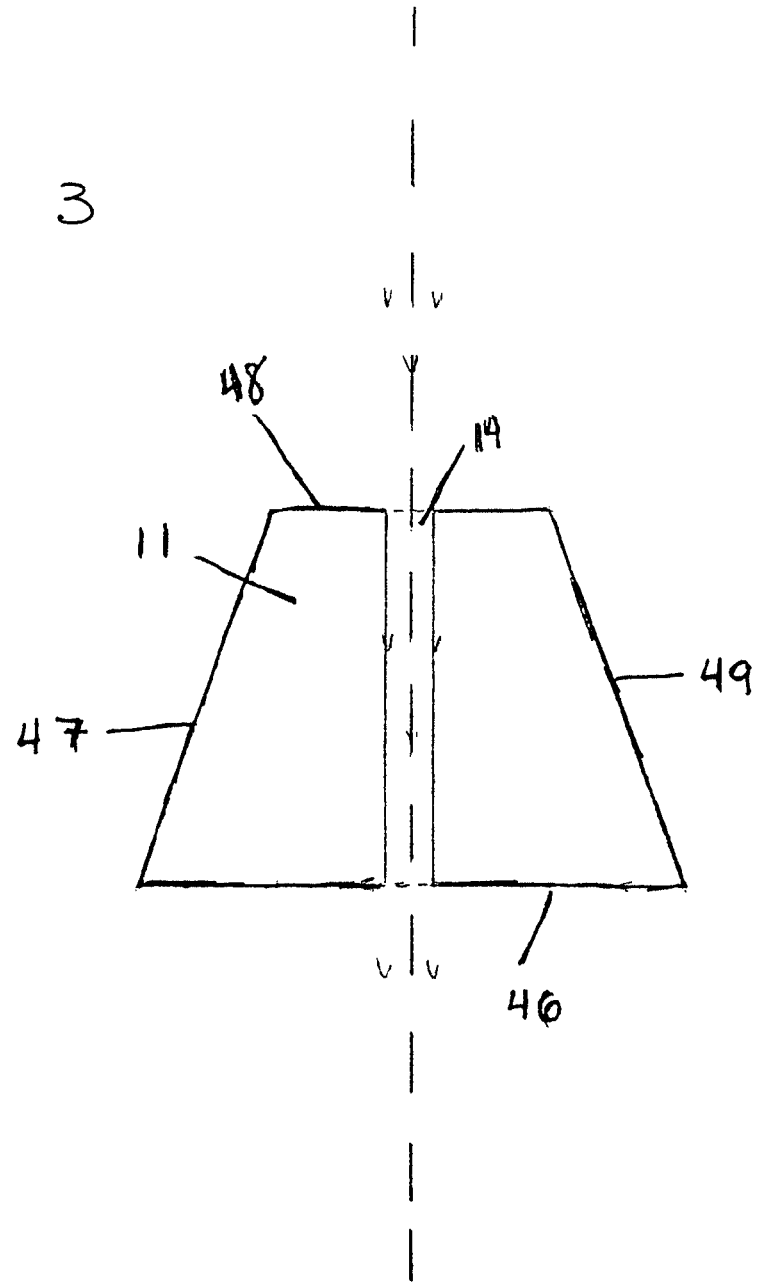

SUBSTANCE DETECTION DEVICE UTILIZING A CYCLONE PARTICLE SEPARATOR

CROSS-REFERENCE TO RELATED PATENT APPLICATIONS

UK (GB) Priority Patent Application 0724127.6, a United Kingdom patent application filed under the "Applicant(s)/contact point" name of SMITHS DETECTION-WATFORD LIMITED" on Dec. 11, 2007, disclosing a cyclone, including the specification, drawings, claims and abstract, is incorporated herein by reference in its entirety.

BACKGROUND

Detectors for detecting chemical substances are known.

Apparatuses for and methods of performing an analysis of a chemical substance, including an analysis utilizing ion mobility spectrometry (IMS), are known. Often, these apparatuses/methods include parameters which enhance an amount of the chemical substance available for analysis, thus improving the macroscopic sensitivity of the analysis. An increased concentration of substance available for analysis, which can be deposited on a membrane of an ion mobility spectrometer (IMS) system, in turn, increases the macroscopic sensitivity of the analysis by allowing additional sample chemicals to pass through the membrane of an IMS system for analysis, due to the additional amounts of sample transferred to the membrane.

Apparatuses for and methods of performing an analysis of a chemical substance often utilize particle separators to separate particles from a gas (such as air). Cyclones, a type of inertial separator, are commonly used to collect atmospheric particles and the like for sampling purposes or filtering, for example: Incoming gas and particles are subjected to cyclonic motion within the cyclone such that the particles separate from the gas due to the differing densities. More specifically, the particles are forced to the wall of the cyclone, which is typically wetted with a sample collection fluid, such as a buffer solution. The particles contact the sample collection fluid and become suspended in it. The sample collection fluid is then collected, and the particles can be analyzed or disposed of, for example. Exemplary cyclones are described in the following patent document publications: See e.g., U.S. Pat. No. 5,918,259, U.S. Pat. No. 6,508,864, Japanese Patent Pub. No. 63-224754, German Patent Pub. No. 2004808, Switzerland Patent Pub. No. 251108, and International Patent Pub. No. WO 2004/065017. As can be seen from these documents, exemplary cyclones can have outlets provided by a tapering, funnel-shape continuation of the inside surface of the cyclone such that the mixture flows internally off the funnel-shape surface.

Cyclones have several limitations. For example, not all of the particles that enter the cyclone are collected. Sample can be aerosolized resulting in loss of sample stored inside the cyclone. Loss of sample reduces particle collection efficiency and requires additional fluid to meet the desired outlet flow rate. The need for large amounts of sample collection fluid can be a significant limitation of current cyclones particularly when the cyclone is to be run for long periods of time, and especially where the cyclone will be run continuously and unattended for long periods of time.

SUMMARY

Accordingly, there is a need for improved cyclone devices that can be used, for example, in the field of analytical instruments, including, but not limited to trace detection of chemical, narcotic, explosive, and biological detection In a first embodiment, there is a substance detection device, comprising a chemical substance analyzer, including, an ion mobility spectrometer, a desorber, a conduit, and a membrane, wherein the membrane extends across a cross-section of the conduit, wherein the membrane is positioned to have a desorber side in gas communication with the desorber and an analysis side opposite the desorber side, wherein the substance detection device is adapted to direct a portion of a chemical substance to the desorber through the conduit so that at least a portion of the entrained chemical substance is transferred to the membrane by interacting with the desorber side of the membrane, wherein the membrane is adapted to diffuse at least a portion of the chemical substance transferred to the membrane through the membrane to the analysis side; and a particle separator, including, a cyclone including a collection chamber having an end, wherein a particle outlet is located at the end of the collection chamber, wherein an internal surface of the collection chamber at the end of the collection chamber is in the form of a protuberance extending into the collection chamber, and wherein the particle outlet is located on the protuberance, wherein the outlet is in fluid communication with the conduit such that particles directed through the outlet travel through the conduit and chemical substances which can be on those particles directed through the outlet are transferred to the membrane by interacting with the desorber side of the membrane.

In another embodiment there is a cyclone that addresses limitations in conventional cyclones by improving particle collection efficiency and/or reducing the amount of sample collection fluid required.

One embodiment relates to a cyclone comprising a chamber, an injector, and a gas exhaust tube. The chamber has at least one closed end. One end of a passage connects to the chamber. The injector provides fluid to the passage. The gas exhaust tube passes gas out of the cyclone. The chamber includes the gas exhaust tube. An internal surface of the at least one closed end of the chamber includes a protuberance. The protuberance includes a particle outlet.

According to another embodiment, a method for collecting particles in a cyclone is provided. The method comprises supplying the cyclone with a gas containing particles, causing a particle to become entrapped in a sample collection fluid to generate a particle-sample collection fluid mixture, moving the mixture in a first direction, moving the particle-mixture to move in a second direction that is substantially opposite of the first direction, and collecting the mixture.

In an exemplary embodiment, there is provided a cyclone including a generally cylindrical chamber having an inlet towards a first end for particulate bearing sample gas, a device for supplying a liquid to the cyclone to wet an internal wall of the cyclone, an outlet towards an opposite, second end of the chamber for collected particles and liquid, and a gas outlet tube extending concentrically along the chamber from the first end such that the sample gas moves in a cyclone manner within the chamber with particles becoming entrapped in the liquid and passing to the particle outlet and gas passing out of the cyclone via the outlet tube, the particle outlet being provided in a tapering surface formation at the second end of the chamber projecting towards the first end of the chamber such that fluid supplied to the chamber flows in a first direction from the first to the second end of the chamber and then flows in the opposite direction over the particle outlet surface formation (protuberance). In some embodiments, the surface formation is preferably substantially conical and can have a flat end surface surrounding an opening to the particle outlet.

In another embodiment, there is provided a cyclone including a generally cylindrical chamber having an inlet towards a first end through which particulate bearing sample gas can enter, a device for supplying a liquid to the cyclone to wet an internal wall of the cyclone, an outlet towards an opposite, second end of the chamber for collected particles and liquid, and a gas outlet tube extending concentrically along the chamber from the first end such that the sample gas moves in a cyclone manner within the chamber with particles becoming entrapped in the liquid and passing to the particle outlet and gas passing out of the cyclone via the outlet tube, the particle outlet being provided in a protuberance at the second end of the chamber projecting towards the first end of the chamber such that fluid supplied to the chamber flows in a first direction from the first to the second end of the chamber and then flows in the opposite direction over the outside of the protuberance and to the particle outlet.

In one embodiment, there is a cyclone comprising a chamber having at least one closed end, wherein one end of a passage connects to the chamber, an injector for providing fluid to the passage, and a gas exhaust tube for passing gas out of the cyclone, wherein the chamber includes the gas exhaust tube, wherein an internal surface of the at least one closed end of the chamber includes a protuberance and wherein the protuberance includes a particle outlet.

In another embodiment, there is a cyclone as disclosed above and/or below, wherein the chamber is cylindrical. According to another embodiment, there is a cyclone as disclosed above and/or below, wherein the chamber has a first portion and a second portion, and wherein the diameter of the first portion is larger than the diameter of the second portion.

In another embodiment, there is a cyclone as disclosed above and/or below wherein the gas exhaust tube has a circular cross section and a circular bore extending along its length with a constant internal diameter, and wherein the diameter of the gas exhaust tube is smaller than the diameter of the first portion. In another embodiment, there is a cyclone as disclosed above and/or below, wherein the center of the gas exhaust tube is concentric with the center of the chamber. In another embodiment, there is a cyclone as disclosed above and/or below wherein a first end of the gas exhaust tube is open to the atmosphere. According to another embodiment, there is a cyclone as disclosed above and/or below wherein a first end of the gas exhaust tube connects to a pump. In another embodiment, there is a cyclone as disclosed above and/or below wherein the protuberance has a first side, a second side, a third side, and a fourth side. In another embodiment, there is a cyclone as disclosed above and/or below wherein the first side of the protuberance is parallel to the third side of the protuberance, and wherein the length of the first side of the protuberance is shorter than the length of the third side of the protuberance. In another embodiment, there is a cyclone as disclosed above and/or below, wherein the length of the first side of the protuberance is less than the diameter of the second portion of the chamber such that a first region exists between the ends of the first side of the protuberance and the ends of the second portion of the chamber.

In another embodiment, there is a cyclone as disclosed above and/or below wherein the first region is flat. In another embodiment, there is a cyclone as disclosed above and/or below wherein the first region is curved. In another embodiment, there is a cyclone as disclosed above and/or below wherein the second side of the protuberance and the fourth side of the protuberance are inclined at an angle relative to the longitudinal axis. In another embodiment, there is a cyclone as disclosed above and/or below wherein the particles and the fluid first move in a first direction and then move in a second direction over the protuberance.

In another embodiment, there is a cyclone as disclosed above and/or below wherein the protuberance is substantially conical, and wherein the second side of the protuberance and the fourth side of the protuberance are flat. In another embodiment, there is a cyclone as disclosed above and/or below wherein the protuberance is substantially conical and the second side of the protuberance and the fourth side of the protuberance are convex or concave.

In another embodiment, there is a cyclone as disclosed above and/or below, wherein the protuberance is in the shape of a dome. In another embodiment, there is a cyclone as disclosed above and/or below wherein the third side of the protuberance is flat and surrounds an opening to the particle outlet. In another embodiment, there is a cyclone as disclosed above and/or below wherein the particle outlet is a tube, and wherein the center of the particle outlet is concentric with the center of the chamber. In another embodiment, there is a cyclone as disclosed above and/or below wherein the particle outlet extends from the third side of the protuberance to an external surface of the chamber. In another embodiment, there is a cyclone as disclosed above and/or below wherein the side of the particle outlet that ends at the external surface of the chamber connects to a channel, and wherein the channel extends to a suction device and a particle receptacle.

In another embodiment, there is a cyclone as disclosed above and/or below wherein the cyclone is formed in a block having a first block portion and a second block portion, and wherein the first block portion includes at least the passage and the second block portion includes at least the chamber. In another embodiment as discussed above and/or below, the first block portion is constructed of a metal and the second block portion is constructed of a transparent material. In another embodiment, there is a cyclone as disclosed above and/or below wherein the second block portion includes a slot. In another embodiment, there is a cyclone as disclosed above and/or below wherein the slot aligns with the passage.

In another embodiment, there is a cyclone as disclosed above and/or below, wherein the injector further comprises a needle that projects through the wall of the first end of the block into the passage and wherein the needle connects to a solution.

In another embodiment, there is a method wherein the method is for collecting particles in a cyclone, comprising supplying the cyclone with a gas containing particles; causing a particle to become entrapped in a sample collection fluid to generate a particle-sample collection fluid mixture; moving the mixture in a first direction; moving the particle-mixture to move in a second direction that is substantially opposite of the first direction; collecting the mixture. In another embodiment, there is a method as disclosed above and/or below, wherein the change from the first to the second direction is caused by movement of the mixture over the surface of a protuberance.

In another embodiment of an apparatus as described above and/or below, there is a substance detection device, comprising a chemical substance analyzer, including an ion mobility spectrometer (IMS), a conduit, and a membrane, wherein the membrane extends across a cross-section of the conduit, wherein the membrane is positioned to have one side and an analysis side opposite the one side, wherein the substance detection device is adapted to direct a portion of a chemical substance to the one side through the conduit so that at least a portion of the chemical substance is transferred to the membrane by interacting with the one side of the membrane, wherein the membrane is adapted to diffuse at least a portion of the chemical substance transferred to the membrane through the membrane to the analysis side, and a particle separator, including a cyclone including a collection chamber having an end, wherein a particle outlet is located at the end of the collection chamber, wherein an internal surface of the collection chamber at the end of the collection chamber is in the form of a protuberance extending into the collection chamber, and wherein the particle outlet is located on the protuberance, wherein the outlet is in fluid communication with the conduit such that particles directed through the outlet travel through the conduit and chemical substances which can be on those particles directed through the outlet are transferred to the membrane by interacting with the one side of the membrane.

In another embodiment of a particle separator as described above and/or below, there is a particle separator, comprising a cyclone including a collection chamber having a first side with respect to a longitudinal axis of the collection chamber, wherein a particle outlet is located at the first side of the collection chamber, wherein an internal surface of the collection chamber at the first side of the collection chamber is in the form of a protuberance extending into the collection chamber, and wherein the particle outlet is located on the protuberance.

In another embodiment of a particle separator as described above and/or below, the first side of the collection chamber has a valley surrounding the protuberance, and wherein the particle outlet stands proud of the valley. In another embodiment of a particle separator as described above and/or below, the particle outlet is located at a crest of the protuberance. In another embodiment of a particle separator as described above and/or below, the protuberance is conical. In another embodiment of a particle separator as described above and/or below, the conical protuberance is truncated at a narrow end of the protuberance to have a flat surface, wherein the particle outlet is located on the flat surface of the truncation.

In another embodiment of a particle separator as described above and/or below, the collection chamber is adapted to rotate about a rotation axis, and wherein the particle outlet is substantially aligned on the rotation axis. In another embodiment of a particle separator as described above and/or below, the collection chamber is an elongated chamber including an inlet adapted to receive a particulate bearing sample gas, wherein the collection chamber is adapted to swirl the particulate bearing sample gas about a rotation axis of the collection chamber such that a fluid slurry including sample particles flows in a first direction with respect to rotation axis towards the first side of the chamber having the protuberance, and then reverses direction to flow over the protuberance and into the particle outlet.

In another embodiment of a particle separator as described above and/or below, the particle outlet is provided on a tapered surface of the protuberance. In another embodiment of a particle separator as described above and/or below, there is a particle separator that further comprises a gas outlet conduit extending inside the collection chamber from an end of the collection chamber opposite the first side with the protuberance, wherein the particle separator is adapted to drive the sample gas in a cyclone manner within the chamber with sample particles becoming entrapped in a liquid supplied to the collection chamber which migrates, with the entrapped sample particles, towards the particle outlet, and drives gas out of the collection chamber through the gas outlet conduit.

In another embodiment of a particle separator as described above and/or below, there is a particle separator that further comprises a device adapted to supply a sample collection fluid supplied to the collection chamber to wet an internal wall of the collection chamber with the sample collection fluid, wherein the sample collection fluid is the liquid supplied to the collection chamber.

In another embodiment of a particle separator as described above and/or below, the liquid entrapping the sample particles flows in a first direction along an axis of rotation of the liquid towards the first side of the chamber having the protuberance, and then reverses direction to flow over the perturbation and into the particle outlet.

In another embodiment of a particle separator as described above and/or below, the collection chamber has an inner bore which is closed by a lateral wall at the first side, except for a particle outlet passage which includes the particle outlet extending from the particle outlet through the lateral wall, forming a substantially flat surface from which the protuberance extends to project into the bore away from the first side. In another embodiment of a particle separator as described above and/or below, the protuberance extends abruptly from the substantially flat surface. In another embodiment of a particle separator as described above and/or below, the protuberance extends in a continuous curve from the substantially flat surface.

In another embodiment of a particle separator as described above and/or below, the protuberance is in the form of a sloping circular wall that extends from the substantially flat surface at about a 135° angle from the substantially flat surface towards a longitudinal axis of the collection chamber about the longitudinal axis. In another embodiment of a particle separator as described above and/or below, a particle outlet passage extends from a center of a top of the protuberance through the lateral wall, the particle outlet passage being in fluid communication with a suction device adapted to suck sample particles through the particle outlet and down the particle outlet passage. In another embodiment of a particle separator as described above and/or below, the particle separator is adapted to spin a sample fluid, containing sample particles, located in the collection chamber about a rotational axis of the collection chamber, and accrete sample particles about the protuberance so that a level of the accreted sample particles, with respect to the longitudinal axis, becomes higher than the particle outlet, so that sample particles are forced to travel through the particle outlet and thus exit the collection chamber.

In another embodiment of a particle separator as described above and/or below, the gas outlet conduit has a substantially constant internal diameter, with an end of the gas outlet conduit facing the protuberance tapering internally to form a flared opening. In another embodiment of a particle separator as described above and/or below, there is a particle separator further including a liquid dispenser adapted to dispense a sample collection fluid into the cyclone.

In another embodiment of a method of collecting particles in a cyclone, there is a method as described above and/or below, which includes supplying the cyclone with a gas containing a particle, causing a particle to become entrapped in a sample collection fluid to generate a particle-sample collection fluid mixture, moving the particle-sample collection fluid mixture in a first direction, moving the particle-sample collection fluid mixture to move in a second direction that is a reverse of the first direction, and collecting the particle-sample collection mixture. In another embodiment of a method of collecting particles in a cyclone, there is a method as described above and/or below, which further includes moving the particle-sample collection mixture in a third direction that is a reverse of the first direction. In another embodiment of a method of collecting particles in a cyclone, there is a method as described above and/or below, wherein the change from the first to the second direction is caused by movement of the mixture over a surface of a protuberance. In another embodiment of a method of collecting particles in a cyclone, there is a method as described above and/or below, wherein the second direction is substantially opposite from the first direction.

It is to be understood that both the foregoing general description and the following detailed description are exemplary and explanatory only and are not restrictive of the embodiments as claimed.

BRIEF DESCRIPTION OF THE DRAWINGS

The accompanying drawings, which are incorporated in and constitute a part of this specification, illustrate embodiments and, together with the description, serve to explain the principles of what is claimed.

FIG. 3 is a sectional side elevation view of a protuberance that acts as a particle surface formation arranged to redirect flow of a fluid.

DETAILED DESCRIPTION OF THE PREFERRED EMBODIMENTS

Figure 1:
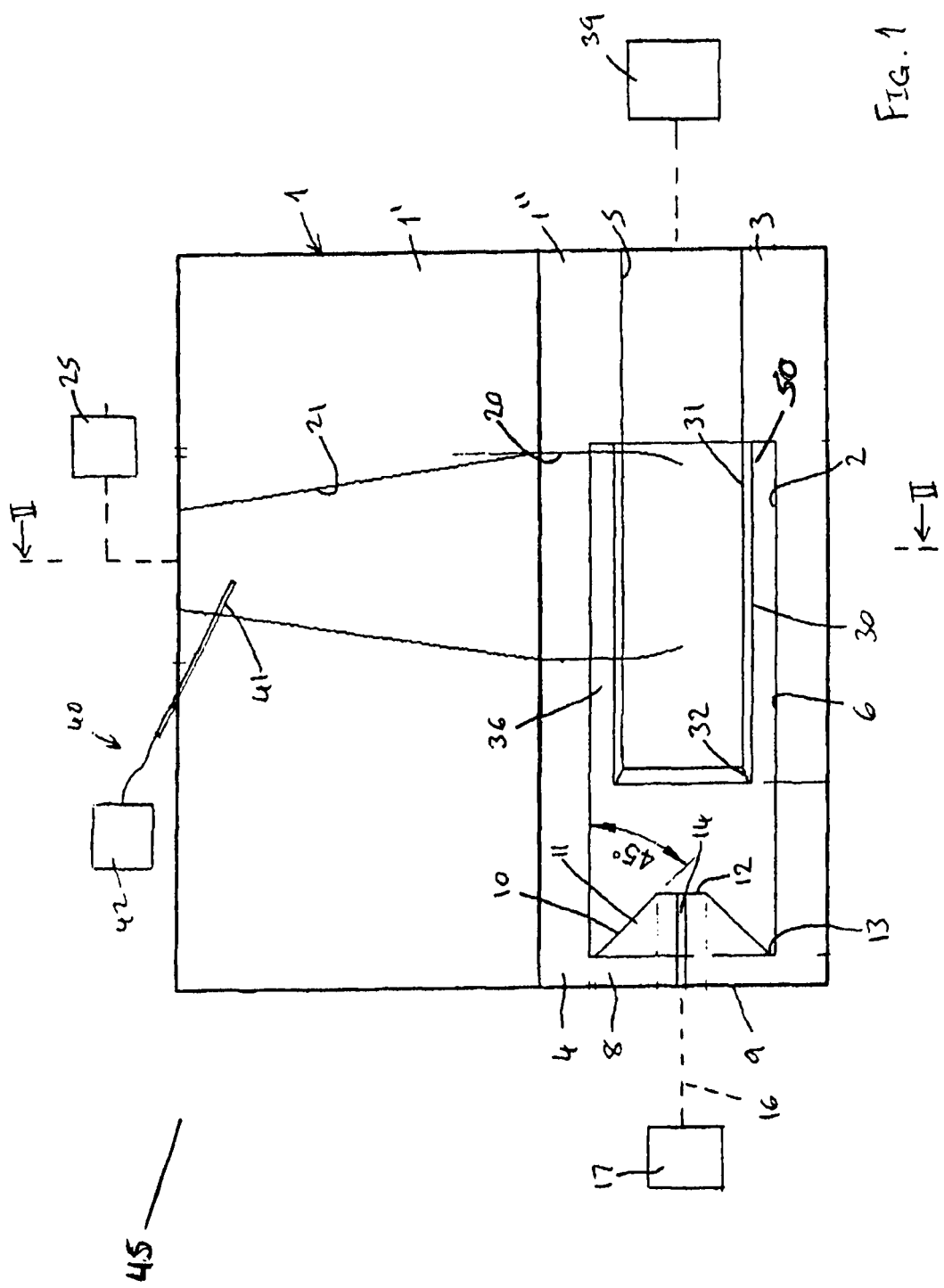
FIG. 1 is a sectional side elevation view of a cyclone embodiment.
Figure 2:
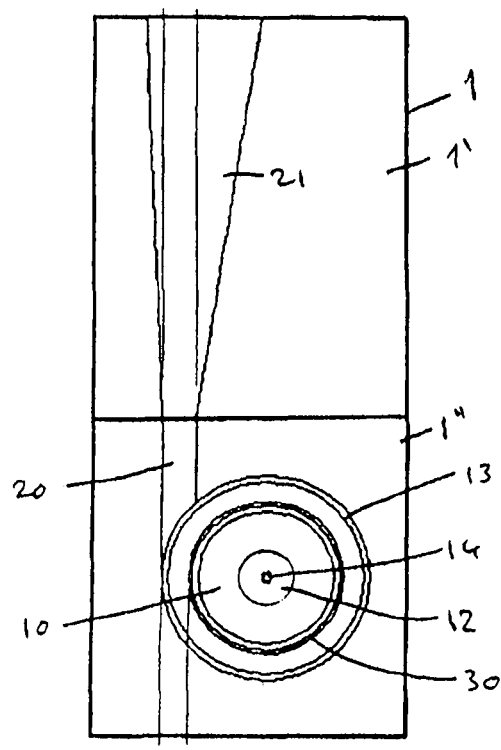
FIG. 2 is a cross-sectional view along the line II-II of the cyclone of FIG. 1.

Unless otherwise specified, "a" or "an" can refer to one or more. For example, "an outlet" can refer to "one or more outlets" unless otherwise specified.

Unless otherwise specified, the description of one or more components does not preclude additional components. For example, the description of an apparatus including A, B, and C includes an apparatus including A, B, C, and D.

Unless otherwise specified, "and" and "or" are used interchangeably. For example, a device having "A or B" can have both "A" and "B," and a device having "A and B" can have only "A" or "B."

In a first embodiment, there is a substance detection device that includes a chemical substance analyzer. In an exemplary embodiment, the chemical substance analyzer includes an ion mobility spectrometer (IMS), a desorber, a conduit, and a membrane. By way of example only and not by way of limitation, the membrane extends across a cross-section of the conduit, wherein the membrane is positioned to have a desorber side in gas communication with the desorber and an analysis side opposite the desorber side. In this exemplary embodiment, the substance detection device is adapted to direct a portion of a chemical substance to the desorber through the conduit so that at least a portion of the entrained chemical substance is transferred to the membrane by interacting with the desorber side of the membrane. In some embodiments, the membrane is adapted to diffuse at least a portion of the chemical substance transferred to the membrane through the membrane to the analysis side. This exemplary embodiment can also include a particle separator, including a cyclone that in turn includes a collection chamber having an end, wherein a particle outlet is located at the end of the collection chamber, wherein an internal surface of the collection chamber at the end of the collection chamber is in the form of a protuberance extending into the collection chamber, and wherein the particle outlet is located on the protuberance. In this embodiment, the outlet is in fluid communication with the conduit such that particles directed through the outlet travel through the conduit and chemical substances which can be on those particles directed through the outlet are transferred to the membrane by interacting with the desorber side of the membrane.

This application also provides a sample collection device comprising a cyclone where a sample collection fluid (e.g., a buffer solution) entrapping sample particles is made to reverse its direction of travel. The cyclone can include a chamber with an inlet towards a first end for particulate bearing sample gas, a device adapted to supply a sample collection fluid to the cyclone to wet an internal wall of the cyclone, an outlet towards an opposite, second end of the chamber for collected sample particles and sample collection fluid, and a gas outlet conduit. The gas outlet conduit can extend along the chamber. The gas can move in a cyclone manner within the chamber where particles can become trapped in the sample collection fluid. The sample collection fluid can then be passed to an outlet, referred to here as a particle outlet. The particle outlet can be part of a surface formation over which the mixture flows causing the fluid to flow in an opposite direction, such as when the fluid is spinning about a rotation axis of the cyclone chamber. In this embodiment, fluid supplied to the cyclone chamber flows in a first direction and then flows in an opposite direction over a surface formation. The surface formation can be located in any suitable location. In one embodiment, the surface formation is located at, near, adjacent to, or in proximity to a particle outlet. In another embodiment, the surface formation can be a protuberance. The protuberance can be any suitable shape, such as, for example, conical, domed, fluted, or formed with a spiral. The surface formation can be, for example, a substantially conical protuberance with a substantially flat end surface in proximity to an opening in a particle outlet tubing. Reversing the direction of sample collection fluid flow, efficiency of particle collection can be increased. In some embodiments, the efficiency can be increased by over approximately 10%, over approximately 15%, or over approximately 20%. In an embodiment, the efficiency of particle collection is increased by around 18%. Increased particle capture efficiency can allow reduction of the sample collection fluid feed flow rate. In some embodiments, the sample collection fluid feed flow rate can be reduced by at least approximately 10%, at least approximately 15%, or at least approximately 20%. In one embodiment, the sample collection fluid feed flow rate is reduced by 19%. Thus, the cyclone described herein can reduce the amount of sample collection fluid needed.

According to an embodiment, shown in FIGS. 1 and 2, a cyclone 45 has a bore 2, an injector 40 to supply sample collection fluid to the cyclone 45, and a gas exhaust tube 30. In some embodiments, the bore 2 includes a gas exhaust tube 30 and a protuberance 11. The chamber 30 passes gas out of the cyclone 45. The protuberance 11 includes a particle outlet 14.

The bore 2 can be any suitable structure that will permit particle separation to take place. The bore 2 can be cylindrical, conical, or any other suitable shape. The bore 2 can, optionally, include a first portion 5 and a second portion 6 that divides the bore 2 into two portions. The first portion 5 and the second portion 6 of the bore 2 can be any suitable structure. For example, the first portion 5 and the second portion 6 of the bore 2 can be cylindrical or one of the portions can be cylindrical and the other conical. The first portion 5 of the bore 2 can include a first end 3. The second portion 6 of the bore 2 can include a second end 4. The first portion 5 and the second portion 6 of the bore 2 can have different diameters. The diameter of the second portion 6 of the bore 2 can be greater than the diameter of the first portion 5 of the bore 2. The first portion 5 of the bore 2 and the second portion 6 of the bore 2 can be any length. A wide range of lengths and diameters are possible for the first portion 5 and the second portion 6 of the bore 2. For example, the length of the first portion 5 of the bore 2 can be about 10 mm, about 20 mm, about 30 mm, or about 40 mm. The diameter of the first portion 5 of the bore 2 can be about 13 mm, about 15 mm, about 20 mm, or about 25 mm. The length of the second portion 6 of the bore can be about 50 mm, about 70 mm, about 80 mm, or about 100 mm. The diameter of the second portion 6 of the bore 2 can be about 25 mm, about 28 mm, about 31 mm, or about 33 mm. In an embodiment, the second portion 6 of the bore is about 87 mm long, plus or minus about 5 mm or 10 mm, and has a diameter of about 31 mm, plus or minus about 3 mm or 6 mm, and the first portion 5 of the bore is about 30 mm long, plus or minus about 3 mm or 6 mm, and has a diameter of about 20 mm, plus or minus about 3 mm or 5 mm.

One end of the bore 2 can be closed. For example, the second end 4 of the bore 2 can be closed by a wall 8, as illustrated in FIG. 1. The wall 8 can include an external surface 9 and an internal surface 10. The external surface 9 of the wall 8 can be any suitable shape. For example, the external surface 9 can be flat, convex, or concave. According to one embodiment, as shown in FIG. 1, the external surface 9 of the wall 8 is flat. The internal surface 10 of the wall 8 can be profiled on its inner surface in a specific manner. In one embodiment, the inner surface 10 can include a protuberance 11.

The protuberance 11 can project into the bore 2, as is depicted in FIG. 1. As seen in FIG. 3, the protuberance 11 can have a first side 46, a second side 47, a third side 48, and a fourth side 49. The first side 46 of the protuberance 11 can be substantially parallel to the third side 48 of the protuberance 11. In some embodiments, the shape of the first side 46 can differ from the shape of the third side 48. For example, the third side 48 can dip inwardly towards the particle outlet 14 to form a conical depression in the top of the protuberance 11 while the first side 46 is substantially flat. The length of the first side 46 of the protuberance 11 can be longer than the length of the third side 48 of the protuberance 11. The second side 47 of the protuberance 11 and the fourth side 49 of the protuberance 11 are inclined at an angle. Both the second side 47 and the fourth side 49 make an angle to the longitudinal axis. The angles of the second side 47 and the fourth side 49 can be the same or different angles. In an embodiment, the angle can be approximately 45 degrees, but other angles are possible. For example, the angle can be at least approximately 20 degrees, at least approximately 30 degrees, at least approximately 35 degrees, at least approximately 45 degrees, at least approximately 55 degrees, or at least 60 approximately degrees. The height of the protuberance 11 can be any suitable height. For example, the height can be about 7 mm, about 9 mm, about 10 mm, or about 12 mm. According to one embodiment, the height can be about 10 mm.

One end of the second side 47 of the protuberance 11 connects to the first side 46 of the protuberance 11 while the second end of the second side 47 of the protuberance 11 connects to the third side 48 of the protuberance 11. One end of the fourth side 49 of the protuberance 11 connects to the third side 48 of the protuberance 11 while the second end of the fourth side 49 of the protuberance 11 connects to the first side 46 of the protuberance 11.

The protuberance 11 can include one or more particle outlets 14. The particle outlet 14 is formed axially of the bore 2. In an embodiment, the particle outlet 14 extends from the center of the third side 48 of the protuberance 11 to the external surface 9. The particle outlet 14 can be cylindrically shaped or of any other suitable shape, such as conically shaped. The end of the particle outlet 14 that coincides with the external surface 9 of the wall 8 is connected to a first channel 16, which can be formed from any suitable material. For example, the first channel can be formed from metallic pipe, plastic tubing, plastic pipe (such as PVC, CPVC, PE, PEX, PB, or ABS), or any other suitable material. The first channel 16 extends to a particle receptacle 17. The particle receptacle 17 can be any suitable receptacle. In some embodiments, a suction device is included such as to draw particles containing fluid from the particle outlet 14 through the first channel 16 and into the particle receptacle 17. The suction device can be any suitable mechanism. For example, the suction device can be a pump.

The center of the first side 46 of the protuberance 11 can be concentric with the center of the particle outlet 14. Both the first side 46 of the protuberance 11 and the center of the particle outlet 14 can be concentric with the bore 2.

The length of the first side 46 of the protuberance 11 can be shorter than the diameter of the second portion 6 of the bore 2. A first region 13 can exist between either end of the first side 46 of the protuberance 11 and either end of the second portion 6 of the bore 2. The first region 13 can be flat, but it can also be any other suitable shape. For example, the first region 13 can be curved.

According to one embodiment, the protuberance 11 is substantially conical. The second side 47 and the fourth side 49 of the protuberance 11 can be any suitable shape. For example, the second side 47 and the fourth side 49 of the protuberance 11 can be flat, convex, or concave. According to another embodiment, the protuberance 11 is dome shaped. The second side 47 and the fourth side 49 of the protuberance 11 can be any suitable shape. For example, the second side 47 and the fourth side 49 of the protuberance 11 can be flat, convex, or concave. Alternatively, the protuberance 11 can be fluted or formed with a spiral formation while the second side 47 and the fourth side 49 of the protuberance 11 can be any suitable shape. For example, the second side 47 and the fourth side 49 of the protuberance can be flat, convex, or concave. The protuberance 11 can also consist of other surface formations while the second side 47 and the fourth side 49 of the protuberance 11 can be any of a number of shapes.

A number of embodiments of protuberance 11 have been described, but other configurations are possible. The protuberance 11 should not be limited to any particular shape or configuration. Rather, the protuberance 11 allows the sample collection fluid-particle mixture to change directions as compared to the direction it moves through the chamber 30. Specifically, the sample collection fluid-particle mixture flows in a first direction from the first to the second end of the bore 2 and then flows in an opposite direction over the particle outlet 14.

The location of the protuberance 11 is not limited to the second end 4 of the bore 2. In an alternate embodiment, the protuberance 11 is located at the first end 3 of the bore 2 and the first end 3 of the bore 2 is closed. Moreover, there can be more than one protuberance 11. Multiple protuberances 11 can be connected to one or more channels 16 and receptacles 17. For example, multiple protuberances 11 can each have a channel 16 which converge into a single receptacle 17. Alternatively, each channel 16 can lead to a different receptacle 17. In some embodiments, there are at least two protuberances, at least three protuberances, at least four protuberances, or at least five protuberances.

Any suitable conduit can be used to allow gas to exit the cyclone 45. For example, the gas exhaust tube 30 is configured to allow gas to exit the cyclone 45. The gas exhaust tube 30 can include a gas external chamber 50 and a gas internal chamber 31. The gas exhaust tube 30, the gas internal chamber 31, and the gas external chamber 50 can be any structure. In an embodiment, the gas exhaust tube 30 has a circular cross section and the gas internal chamber 31 is circular. The gas exhaust tube 30 and gas internal chamber can be any other suitable shape, such as conically shaped, and they can have the same or different shapes. The diameter of the gas internal chamber 31 and the length of the gas exhaust tube 30 can be any suitable diameter and length respectively. For example, the diameter of the gas internal chamber 31 can be about 15 mm, about 18 mm, about 20 mm, or about 25 mm. The length of the gas exhaust tube 30 can be about 52 mm, about 55 mm, about 58 mm, or about 63 mm. In one embodiment, the diameter of the gas internal chamber 31 can be 20 mm, and the gas exhaust tube 30 can be 58 mm long.

The gas exhaust tube 30 can be located anywhere in the bore 2. Preferably, the gas exhaust tube 30 is located in the second portion 6 of the bore 2. The first end 32 of the gas exhaust tube 30 can taper internally to form a flared opening to the gas exhaust tube 30. It is possible for either end of the gas exhaust tube 30 to taper internally and form a flared opening. In an embodiment, the first end 32 of the gas exhaust tube 30 is the end closest to the protuberance 11. The first end 32 of the gas exhaust tube 30 can be located between a slot 20 and the particle outlet 14, and located at a point spaced from the slot 20.

The gas external chamber 50 can be any diameter that is smaller than the diameter of the bore 2. A wide range of diameters are possible for the gas external chamber 50. For example, the diameter of the gas external chamber 50 can be less than about 18 mm, less than about 23 mm, less than about 28 mm, or less than about 40 mm. In an embodiment, the diameter of the gas external chamber 50 is about 23 mm. An annular recess 36 can exist between the gas external chamber 50 and the external sides of the bore 2. The annular recess 36 has a width equal to the diameter of the bore 2 minus the diameter of the gas external chamber 50. For example, if the diameter of the bore 2 is 27 mm and the diameter of the gas external chamber 50 is 23 mm, the width of the annular recess 36 is 4 mm. A wide range of diameters are possible for the bore 2 and the chamber 50. For example, the diameter of the bore 2 can be less than about 18 mm, less than about 23 mm, less than about 28 mm, or less than about 40 mm. The diameter of the chamber 50 can be less than about 28 mm, less than about 23 mm, less than about 18 mm, less than about 15 mm, and less than about 10 mm. A wide range of widths are possible for the annular recess 36. For example, the width of the annular recess 36 can be less than about 2 mm, less than about 4 mm, less than about 6 mm, and less than about 12 mm.

The open end of the gas exhaust tube 30 can open to the atmosphere. In one embodiment, the second end of the gas exhaust tube 30 is open. The second end of the gas exhaust tube 30 can open to the first portion 5 of the bore 2. The first portion 5 of the bore 2 opens to the atmosphere. Alternatively, the second end of the gas exhaust tube 30 can connect to a first pump 39.

The cyclone can include an injector 40 for providing fluid to a passage 21. The injector 40 can provide any fluid to the passage 21. In one embodiment, the fluid is a buffer solution used to capture particles. The injector 40 can include a needle 41. The needle 41 can connect to a supply 42 that contains the liquid to be provided. The needle 41 projects through the wall of a block 1 and into the passage 21. While the figures show only one injector 40 and supply 42, there can be more than one injector 40 connected to either one or multiple supply 42. For example, a single injector 40 can be connected to a plurality of supply 42 that each contains a different fluid. Alternatively, there can be multiple injectors 40 that are connected to the same or different supply 42. The fluid can be dispensed in any manner. For example, the fluid can be provided to the passage 21 in the form of a mist, aerosol, or steady flow. The fluid can be added at different locations of the cyclone 45.

The block 1 includes the cyclone 45. The block can include a first block portion 1' and a second block portion 1". The first block portion 1' and the second block portion 1" can be made of any suitable materials, including metals, plastics, or some combination thereof, for example. In an embodiment, the first block portion 1' is made of a metal. For example, the first block portion 1' can be made of aluminum and/or steel, and/or alloys thereof. In an embodiment, the second block portion 1" is made of a transparent material, such as a transparent plastic. Examples of suitable materials include Perspex, Plexiglass, Vitroflex, or Limacryl. The block 1 can be any suitable shape. For example, the block 1 can be rectangular, square, or cylindrical. In an embodiment, as shown in FIG. 1, the block 1 is rectangular. The rectangular block 1 can be any suitable length, height, and depth. For example, the block 1 can be about 100 mm long, about 110 mm long, about 120 mm long, or about 130 mm long. The block 1 can be about 90 mm high, about 100 mm high, about 110 mm high, or about 120 mm high. The block 1 can be about 30 mm deep, about 35 mm deep, about 45 mm deep, or about 55 mm deep. In an embodiment, the block 1 is about 120 mm long, about 110 mm high, and about 45 mm deep.

The first block portion 1' can include at least the passage 21 and the second block portion 1" can include at least the bore 2. The second block portion 1" can also include a slot 20. The slot 20 can extend into the first block portion 1'.

The slot 20 can be located anywhere along the bore 2. In an embodiment, the slot 20 is located to the left of the junction between the first portion 5 and the second portion 6 of the bore 2. The slot 20 can be any length and width. A wide range of lengths and widths of the slot 20 are possible. For example the length of the slot 20 can be about 30 mm, about 35 mm, about 40 mm, or about 45 mm. The width of the slot 20 can be for example, about 3 mm, about 5 mm, about 7 mm, and about 9 mm. In an embodiment, the slot 20 can be about 35 mm long and about 5 mm wide. The slot 20 can extend along the same longitudinal axis as that of the block 1. The edges of the slot 20 can align with the outside of the passage 21.

The passage 21 can be any length and shape. In an embodiment, the passage 21 is about 60 mm long. A wide range of lengths is available for the passage 21. For example, the passage 21 can be about 40 mm long, about 50 mm long, about 60 mm long, or about 70 mm long. In another embodiment, the passage 21 can taper along its length. The passage 21 can be circularly shaped. The thinnest part of the passage 21 can be 17 mm wide. The thinnest part of the passage 21 can be any suitable width. For example, the thinnest part of the passage 21 can be about 15 mm, about 17 mm, about 20 mm, or about 25 mm. The widest part of the passage 21 can have the same width and length as the slot 20. For example, if the widest part of the passage 21 is about 35 mm long and about 5 mm wide, the slot 20 can be about 35 mm long and about 5 mm wide. The widest part of the passage 21 can be any suitable length and width. For example, the widest part of the passage 21 can be about 25 mm long, about 30 mm long, about 35 mm long, or about 40 mm long. The widest part of the passage 21 can be about 3 mm wide, about 5 mm wide, about 7 mm wide, or about 8 mm wide. The slot 20 can be any suitable length and width. For example, the slot 20 can be about 25 mm long, about 30 mm long, about 35 mm long, or about 40 mm long. The slot 20 can be about 3 mm wide, about 5 mm wide, about 7 mm wide, or about 8 mm wide.

An end of the passage 21 connects to a source containing gas and particles. The gas can be ambient air. A second pump 25 can pump the gas and particles into the passage 21. Alternatively, the second pump 25 and the first pump 39 can simultaneously operate to pump the gas and particles into the cyclone 45 by suction. According to one embodiment, only the first pump 39 pumps the gas into the cyclone 45; the second pump 25 is not used.

In operation, the gas and particles flow along the passage 21. While in the passage 21, the gas and the particles mix with the fluid from the injector 40. The mixture of the gas, the particles, and the fluid enter the bore 2 through the annular recess 36. The mixture flows in a circular, swirling motion around the inside of the bore 2. The fluid wets the surface of the bore 2. The difference in density between the particles and the gas combined with the centripetal force caused by the rotating movement, allows the particles to separate from the gas. As the gas moves into the area between the first end 32 of the gas exhaust tube 30 and the second end 4 of the bore 2, the gas begins to move in a second direction. Initially, the gas moves in a first direction. The first direction can be a movement toward the second end 4 of the bore 2. The second direction is opposite that of the first direction. When the gas moves in the second direction, the gas moves through the annular recess 36. The gas can then exit the annular recess 36 and enter the atmosphere. While the gas moves in the second direction, the particles and the fluid continue to move in the first direction. When the particles and the fluid reach the first region 13, they begin to move in the second direction. The particles and the fluid flow in a radial motion externally over the protuberance 11. When the fluid and particles reach the ends of the third side 48 of the protuberance 11, the fluid and the particles move over the third side 48 of the protuberance 11 and collect around the particle outlet 14. The particle receptacle 17 can apply suction continuously to move the mixture into the particle outlet 14 and out to the particle receptacle 17 for analysis. Particles can be taken from the receptacle 17 to an analyzer or detector for analysis. In an alternative embodiment, the particles can directly move to an analyzer or detector.

According to another embodiment, the bore 2 does not include a protuberance 11. Instead, the bore 2 includes a tapering surface formation at the second end 4 of the bore 2 such that fluid and particles entering the bore 2 move in the first direction and then move in the second direction over the protuberance 11.

Some exemplary scenarios detailing use of some embodiments will now be described.

With reference first to FIG. 1, an exemplary particle separation device 1 is first employed. Specifically, the exemplary particle separation device employed is a cyclone formed in a rectangular block 1 which, in an exemplary embodiment, is about 120 mm long, 110 mm high and 45 mm deep, although other embodiments can be smaller or larger. The upper part 1' of the block 1 can be machined of a metal, such as aluminum or steel, and the lower part 1" can be made of a transparent material, such as Perspex to allow operation of the cyclone to be viewed. Internally, the lower part 1" of the block has a cylindrical wall or bore 2 extending from its right-hand end 3 but is closed at the left-hand end 4. The bore 2 is divided into two portions 5 and 6 of different diameters. The right-hand portion 5 is about 30 mm long with a diameter of about 20 mm. The left-hand portion 6 extends for approximately 87 mm and has a larger diameter of about 31 mm. At its left-hand end 4 the bore 2 is closed by a lateral wall 8, which presents a flat external surface 9 but is profiled on its inner surface 10.

Specifically, the inner surface 10 is provided by a protuberance 11, which projects into the bore 2, towards the right-hand end 3 of the cyclone. The protuberance 11 is substantially conical apart from a flat top 12 of diameter of about 8 mm. The diameter of its base is slightly less than the internal diameter of the bore 2 so that a flat annular floor 13 is formed between the outer edge of the protuberance 11 and the inside of the barrel bore. This region of the junction between the inner wall 2 of the barrel 1 and the protuberance 11, in some embodiments, has a curved, continuous transition rather than an abrupt transition. The sloping wall of the protuberance 11 is inclined at an angle of 45° to the longitudinal axis and its height is about 10 mm. A particle outlet passage 14 is formed axially of the bore 2 through the wall 8, extending from the centre of the top 12 of the conical protuberance 11 to the external surface 9. At its external end the passage 14 is connected to one end of tubing 16 extending to some form of suction device and particle receptacle 17.

In the exemplary scenario, in the exemplary separation device depicted in FIG. 1, the lower part 1" of the block 1 is also provided with a side inlet aperture in the form of an elongate slot 20 formed through its wall just forwardly of (with respect to the Figure, to the left of) the junction between the forward and rear portions 5 and 6 of the bore 2. The slot 20 is about 35 mm long and 5 mm wide and extends longitudinally of the barrel. The slot 20 aligns with a gas sample inlet passage 21 extending laterally outwards in the upper part V. The passage 21 is about 60 mm long and tapers along its length being circular in shape and with a diameter of about 17 mm at its outer end and being of elongate section at its inner end with a length 35 mm and a width of 5 mm to match the shape and size of the slot 20. In use, the outer end of the passage 21 is connected to a source of gas to be sampled, such as ambient air, via a pump 25 operable to blow the gas into the cyclone via the passage 21.

In the exemplary scenario, the obtained exemplary separation device depicted in FIG. 1 includes a cyclone that also has a gas exhaust tube 30 secured, with respect to FIG. 1, in the left-hand end 6 of the bore 2. The exhaust tube 30 is about 58 mm long, is of circular cross section, and has a circular bore 31 extending along its length with a constant internal diameter of about 20 mm forming a smooth continuation of the right-hand portion, with respect to FIG. 1, 5, of the bore 2. The left-hand, inlet end 32 of the bore 31 tapers internally to form a flared opening to the tube 30. The left-hand, inlet end 32 of the exhaust tube 30 is located along the bore 2 at a point spaced from the gas inlet slot 20 and between this slot and the particle outlet passage 14. Externally, the exhaust tube 30 has a diameter of about 23 mm leaving an annular recess 36 with a width of about 4 mm between the outside of the exhaust tube and the bore 2. The rear end of the exhaust tube 30 opens to atmosphere via the right-hand portion 5 of the bore 2. Alternatively, the exhaust tube 30 can be connected to a pump 39 in addition to, or instead of the pump 25 at the inlet passage 21 so that the sample gas is drawn into the cyclone by suction.

In the exemplary scenario, the obtained exemplary separation device includes a cyclone that includes a liquid injector 40 by which a buffer solution is added to the cyclone. In the present example, the liquid injector 40 is shown in FIG. 1 as having a needle 41 projecting through the wall of the block 1 into the passage 21, the needle being connected to a supply 42 of the buffer solution. In some embodiments, the buffer solution can be added at different locations.

In the exemplary scenario, during operation of the obtained exemplary separation device, the gas with any suspended particles flows along the inlet passage 21 where it mixes with the buffer solution dripping from the injector needle 41. The mixture of the gas, particles and buffer emerges tangentially into the annular recess 36 around the outside of the exhaust tube 30. The mixture, therefore, flows in a circular, swirling motion around the inside of the bore 2, wetting its surface with the liquid and with the particles separating from the gas as a result of their different densities and the centripetal force caused by the rotating movement. Further gas with particles and buffer solution entering the cyclone causes movement forwardly, to the left with respect to FIG. 1, away from the inlet slot 20, in a spiraling fashion. As the gas moves into the region between the forward end 32 of the exhaust tube 30 and the closed end 4 of the bore 2, it changes direction and flows from left to right, with respect to FIG. 1, along the exhaust tube to atmosphere. The slurry of the buffer solution and suspended particles continues to flow along and around the bore 2 until it reaches the floor 13 where it is forced to flow radially inwardly and rearwardly up over the conical surface 10 of the protuberance 11. When the liquid mixture reaches the peak of the protuberance 11 it flows over its flat top 12 and collects around the outlet 14. Suction is applied continuously or periodically by the particle receptacle 17 to draw the mixture into the receptacle for subsequent analysis. Alternatively the particle mixture can flow directly to some form of known analyzer.

Accordingly, the liquid-particle mixture in the just-described scenario is made to change its direction of travel and/or reverse its direction of travel by the presence of the conical protuberance over which the mixture flows externally. In some embodiments of the separator device 1, the design of the separator device 1 enables the efficiency of particle collection to be increased by up to around 18% while also enabling a buffer feed flow rate to be reduced by 19% giving a saving in buffer usage.

In some embodiments, protuberances of different shape other than that depicted in the Figures/discussed above are used. For example, the slope of the cone need not be flat but can have a convex or concave curvature, and it can be steeper or flatter than described above. The protuberance can alternatively have some other shape, such as a domed shape or it can be fluted or formed with a spiral or other surface formations, provided that the present invention can be practiced.

In an exemplary embodiment, the bore 2 is a collection chamber having an end. In another embodiment, the bore 2 is a collection chamber having a first side with respect to the longitudinal axis of the collection chamber. According to another embodiment the collection chamber has an inner bore 2 which is closed by a lateral wall at the first side.

According to an embodiment, the first channel 16 is a particle outlet passage which includes the particle outlet 14 extending from the particle outlet 14 through the lateral wall 8.

In an exemplary embodiment, the internal surface 10 is an internal wall. In another embodiment, the gas exhaust tube 30 is a gas outlet conduit extending inside the collection chamber 2 from an end of the collection chamber opposite the first side 46 of the protuberance 11.

In an exemplary embodiment, either or both the third side 48 and the first side 46 of the protuberance 11 are a tapered surface. According to another embodiment, either or both the third side 48 and the first side 46 of the protuberance 11 are a crest. In another exemplary embodiment, the third side 48 of the protuberance 11 is a narrow end.

In another exemplary embodiment, the collection chamber 2 is adapted to rotate about a rotation axis, wherein the particle outlet 14 is substantially aligned on the rotation axis.

It is noted that dimensions are provide herein by way of example only and not by way of limitation. In this regard, in some embodiments, the dimensions can vary by plus or minus about 1% to about 100%, or even more. Also, in some embodiments of the invention, the dimensions are uniformly scaled up and/or scaled down.

The embodiments described above have been set forth herein for the purpose of illustration and are exemplary in nature unless otherwise explicitly stated. This description, however, should not be deemed to be a limitation on the scope of the embodiments. This is especially true with respect to various specific dimensions and regimes detailed herein. Various modifications, adaptations, and alternatives may occur to one skilled in the art without departing from the claimed concept.

What is claimed is:

1. A substance detection device comprising:

a chemical substance analyzer comprising:

an ion mobility spectrometer;

a conduit; and a membrane, wherein the membrane extends across a cross-section of the conduit, wherein the membrane is positioned to have one side and an analysis side opposite the one side, wherein the substance detection device is adapted to direct a portion of a chemical substance to the one side through the conduit so that at least a portion of the chemical substance is transferred to the membrane by interacting with the one side of the membrane, wherein the membrane is adapted to diffuse at least a portion of the chemical substance transferred to the membrane through the membrane to the analysis side; and a particle separator comprising:

a cyclone including a collection chamber having a first side with respect to a longitudinal axis of the collection chamber, and a second side with respect to the longitudinal axis of the collection chamber, wherein a particle outlet is located at the first side of the collection chamber, wherein an internal surface of the collection chamber at the first side of the collection chamber is in the form of a protuberance extending into the collection chamber, and wherein the particle outlet extends through the protuberance, wherein the cyclone is configured to cause particles to flow along an inner surface of the collection chamber in a first direction towards the first side of the collection chamber, then flow along an outer surface of the protuberance in a second direction towards the second side of the collection chamber, and then flow through the particle outlet in the first direction, and wherein the outlet is in fluid communication with the conduit such that particles directed through the outlet travel through the conduit and chemical substances which may be on those particles directed through the outlet are transferred to the membrane by interacting with the one side of the membrane.

2. A particle separator comprising:

a cyclone including a collection chamber having a first side with respect to a longitudinal axis of the collection chamber, and a second side with respect to the longitudinal axis of the collection chamber, wherein a particle outlet is located at the first side of the collection chamber, wherein an internal surface of the collection chamber at the first side of the collection chamber is in the form of a protuberance extending into the collection chamber, and wherein the particle outlet extends through the protuberance, and wherein the cyclone is configured to cause particles to flow along an inner surface of the collection chamber in a first direction towards the first side of the collection chamber, then flow along an outer surface of the protuberance in a second direction towards the second side of the collection chamber, and then flow through the particle outlet in the first direction.

3. The particle separator of claim 2, wherein a valley is formed in the first side of the collection chamber between the protuberance and walls of the collection chamber.

4. The particle separator of claim 2, wherein the particle outlet is located at a crest of the protuberance.

5. The particle separator of claim 2, wherein the protuberance is conical.

6. The particle separator of claim 5, wherein the conical protuberance is truncated at a narrow end of the protuberance to have a flat surface, wherein the particle outlet is located on the flat surface of the truncation.

7. The particle separator of claim 2, wherein the collection chamber is adapted to rotate about a rotation axis, and wherein the particle outlet is substantially aligned on the rotation axis.

8. The particle separator of claim 2, wherein the collection chamber is an elongated chamber including an inlet adapted to receive a particulate bearing sample gas, wherein the collection chamber is adapted to swirl the particulate bearing sample gas about a rotation axis of the collection chamber such that a fluid slurry including sample particles flows in a first direction with respect to rotation axis towards the first side of the chamber having the protuberance, and then reverses direction to flow over the protuberance and into the particle outlet.

9. The particle separator of claim 8, wherein the particle outlet is provided on a tapered surface of the protuberance.

10. The particle separator of claim 8, further comprising a gas outlet conduit extending inside the collection chamber from an end of the collection chamber opposite the first side with the protuberance, wherein the particle separator is adapted to drive the sample gas in a cyclone manner within the chamber with sample particles becoming entrapped in a liquid supplied to the collection chamber which migrates, with the entrapped sample particles, towards the particle outlet, and drives gas out of the collection chamber through the gas outlet conduit.

11. The particle separator of claim 10, further comprising a device adapted to supply a sample collection fluid supplied to the collection chamber to wet an internal wall of the collection chamber with the sample collection fluid, wherein the sample collection fluid is the liquid supplied to the collection chamber.

12. The particle separator of claim 10, wherein the liquid entrapping the sample particles flows in a first direction along an axis of rotation of the liquid towards the first side of the chamber having the protuberance, and then reverses direction to flow over the protuberance and into the particle outlet.

13. The particle separator of claim 2, wherein the collection chamber has an inner bore which is closed by a lateral wall at the first side, except for a particle outlet passage which includes the particle outlet extending from the particle outlet through the lateral wall, forming a substantially flat surface from which the protuberance extends to project into the bore away from the first side.

14. The particle separator of claim 13, wherein the protuberance extends abruptly from the substantially flat surface.

15. The particle separator of claim 13, wherein the protuberance extends in a continuous curve from the substantially flat surface.

16. The particle separator of claim 13, wherein the protuberance is in the form of a sloping circular wall that extends from the substantially flat surface at about a 135° degree. angle from the substantially flat surface towards a longitudinal axis of the collection chamber about the longitudinal axis.

17. The particle separator of claim 13, wherein a particle outlet passage extends from a center of a top of the protuberance through the lateral wall, the particle outlet passage being in fluid communication with a suction device adapted to suck sample particles through the particle outlet and down the particle outlet passage.

18. The particle separator of claim 2, wherein the particle separator is adapted to spin a sample fluid, containing sample particles, located in the collection chamber about a rotational axis of the collection chamber, and accrete sample particles about the protuberance so that a level of the accreted sample particles, with respect to the longitudinal axis, becomes higher than the particle outlet, so that sample particles are forced to travel through the particle outlet and thus exit the collection chamber.

19. The particle separator of claim 10, wherein the gas outlet conduit has a substantially constant internal diameter, with an end of the gas outlet conduit facing the protuberance tapering internally to form a flared opening.

20. The particle separator of claim 2, further including a liquid dispenser adapted to dispense a sample collection fluid into the cyclone.

* * * * *